(12) United States Patent
Neubert

(10) Patent No.: US 6,183,086 B1
(45) Date of Patent: Feb. 6, 2001

(54) VARIABLE MULTIPLE COLOR LED ILLUMINATION SYSTEM

(75) Inventor: William J. Neubert, Ballwin, MO (US)

(73) Assignee: Bausch & Lomb Surgical, Inc., Claremont, CA (US)

(*) Notice: Under 35 U.S.C. 154(b), the term of this patent shall be extended for 0 days.

(21) Appl. No.: 09/267,523

(22) Filed: Mar. 12, 1999

(51) Int. Cl.[7] ............................................. A61B 3/10
(52) U.S. Cl. ............................................. 351/221
(58) Field of Search .................. 351/205, 206, 351/211, 212, 221, 242, 243, 246; 359/802; 345/8

(56) References Cited

U.S. PATENT DOCUMENTS

| | | | |
|---|---|---|---|
| 5,500,697 | * 3/1996 | Fujieda | 351/212 |
| 5,734,459 | * 3/1998 | Chang | 351/242 |
| 6,008,781 | * 4/2000 | Furness, III et al. | 345/8 |
| 6,052,239 | * 4/2000 | Matsui et al. | 359/802 |

OTHER PUBLICATIONS

The Photonics Design & Applications Handbook 43rd Edition Laurin Publishing Co., Inc. 1997.

Standard Practice for Computing the Colors of Objects by Using the CIE System American Society for Testing and Materials, May, 1995.

* cited by examiner

Primary Examiner—George Manuel
(74) Attorney, Agent, or Firm—Grant D. Kang; Michael L. Smith

(57) ABSTRACT

An ophthalmic illumination system is provided that emits a light that is controllably variable in color. Because the light originates from LEDs, less heat is generated from the emitted light as compared to conventional ophthalmic illumination systems using tungsten or discharge sources.

5 Claims, 1 Drawing Sheet

VARIABLE MULTIPLE COLOR LED ILLUMINATION SYSTEM

BACKGROUND OF THE INVENTION

1. Field of the Invention

This invention relates to illumination systems that are used in conjunction with ophthalmic surgery for illuminating ocular tissue. More specifically, this invention provides an illumination system that can provide varying color and intensity.

2. Related Art

Currently, illumination systems for illuminating ocular tissue use tungsten, discharge, or fluorescent lamps. These light sources give off a great deal of heat. This heat must be removed by adding cooling fans to the equipment. In addition, because the tungsten and fluorescent lamps convert a significant fraction of the incoming power to heat, a large power supply is required to drive the lamps. The added cooling fans and larger power supply increases the cost of the illumination system.

A tungsten light source has a longevity of approximately 50 hours and produces an extremely bright, hot light.

Ophthalmic surgeons conduct anterior and posterior segment surgery. In general, ophthalmic surgeons will specialize by performing only anterior segment surgery, or by performing only posterior segment surgery. Not surprisingly, due to the variation in tissue and due to the depth of surgery, ophthalmic surgeons have varying preferences on the color of light provided by an illumination system. Ophthalmic surgeons conducting anterior segment surgery have a tendency to prefer an illumination system that will deliver a yellow-red light, while ophthalmic surgeons conducting posterior surgery have a tendency to prefer an illumination system that provides a white-blue light.

In order to accommodate these varying preferences, a rather extensive offering of light filters has been devised to vary the color output of a light source. Thus, one or more light filters must be selected and installed proximate the light source of an illumination system. However, there is variation in the initial color outputs between illumination systems. One tungsten light source may put out an unfiltered light that is slightly different in color from another tungsten light source from the same manufacturer. Thus, what may be the correct filtering choice for a first illumination system may not achieve similar results when the same light filters are installed in a second illumination system. Accordingly, the selection of light filters might not result in the desired color output without some experimentation.

SUMMARY OF THE INVENTION

It is in view of the above problems that the present invention was developed. The invention is a variable, multiple color, LED (light Emitting Diode) ophthalmic illumination system that permits control over variation in color and intensity of the light output. As a additional benefit, less heat is generated because LEDs are highly efficient. In addition, LEDs are more reliable. A tungsten light source will last approximately fifty (50) hours. However, an LED light source has a longevity of approximately 20,000 hours. Due to the configuration of the illumination system of the present invention, control over the color of the light output can be strictly controlled. Stated alternatively, the present invention can control the color of the light output such that a yellower light or a bluer light or a redder light is produced. This control eliminates the necessity of selecting among multiple light sources, depending on the procedure, and among multiple filters. In addition, the present invention provides a lower heat output as compared to ophthalmic illumination systems of the prior art.

Further features and advantages of the present invention, as well as the structure and operation of various embodiments of the present invention, are described in detail below with reference to the accompanying drawings.

BRIEF DESCRIPTION OF THE DRAWINGS

The accompanying drawings, which are incorporated in and form a part of the specification, illustrate the embodiments of the present invention and together with the description, serve to explain the principles of the invention. In the drawings.

DETAILED DESCRIPTION OF THE PREFERRED EMBODIMENTS

Figure 1:
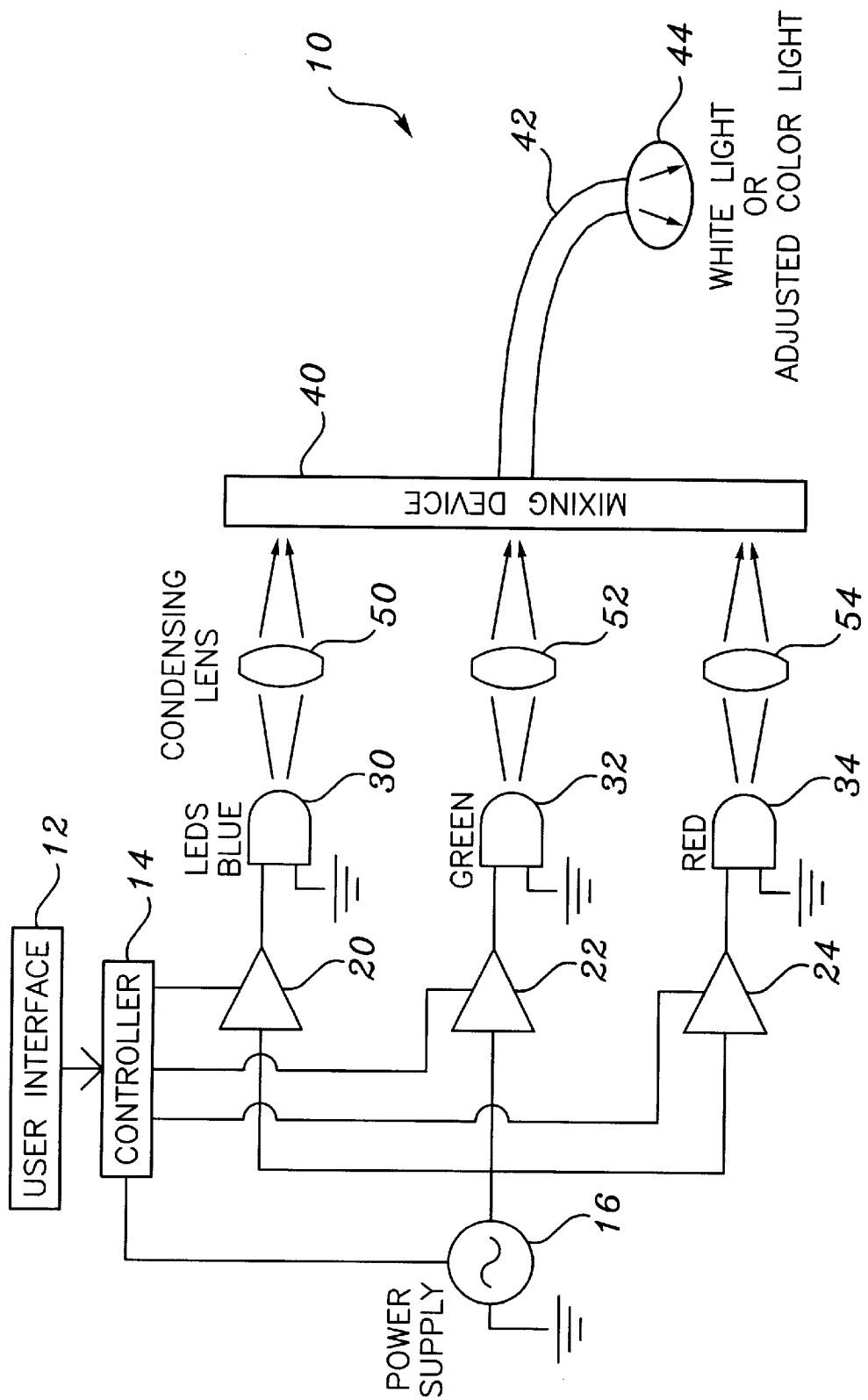
FIG. 1 illustrates a schematic view of the ophthalmic illumination system of the present invention.

Referring to the accompanying drawings in which like reference numbers indicate like elements, FIG. 1 illustrates the ophthalmic illumination system shown generally at 10 of the present invention. The illumination system of the present invention includes user interface 12, controller 14, power supply 16, first power amplifier 20, second power amplifier 22, third power amplifier 24, first light emitting diode (LED) 30, second LED 32, third LED 34, mixing device 40, and exit lightguide 42. Preferably, and thus shown in FIG. 1 but not required, is first condensing lens 50, second condensing lens 52 and third condensing lens 54. Preferably, first LED 30 is a blue LED, second LED 32 is a green LED, and third LED 34 is a red LED. However, other LED colors are conceivable, such as blue, yellow or red. In general, three LEDs or sources of different emitting wavelength are required. It is also conceivable that more than three LEDs or more than three wavelengths may be used.

In operation, a user inputs the desired light intensity and/or color into user interface 12. Based on the demanded light intensity and/or color, controller 14 determines the appropriate power level and amplifier gain for each LED. The determination of the color ratios and intensities that are required to produce a desired color output are well known. The blue, green and red sources are the same color sources that are used to produce color in television sets. Additional discussion of the measurement and analysis of color is provided in The Photonics Design and Applications Handbook (1997), pp. H-52 to H-60, and is hereby incorporated by reference in its entirety. In addition, the determination of the color ratios and intensities that are required to produce a desired color output are provided as a CIE standard, as described in ASTM E308-95 "Standard Practice for Computing the Colors of Objects Using the CIE System" which is hereby incorporated by reference in its entirety.

After determining the proper color ratios and intensities, controller 14 sends power signal to power supply 16, a first gain signal to first power amplifier 20, a second gain signal to second power amplifier 22, and a third gain signal to third power amplifier 24.

As a result, first LED 30, second LED 32, and third LED 34 emit light. Preferably, but not required, the light from first LED 30 is condensed by first condensing lens 50; the light from second LED 32 is condensed by second condensing lens 52; and the light from third LED 34 is condensed by third condensing lens 54. Condensing lenses are used commonly in telecommunications systems and are widely available. Condensing lenses may take many forms, and range from crude single element molded plastic devices to multi-element aspherical precision assemblies. The purpose of a condensing lens is to focus the diffuse light emitted by each LED.

Upon the light's entering and then exiting from the condensing lenses 50, 52, and 54, light enters mixing device 40. Mixing device 40 is any device that will mix light from multiple sources and are well known in the lightguide arts. Examples of mixing device 40 include glass rods, bifurcated or trifurcated fiber optic cables, integrating spheres, or the like.

Upon exiting from mixing device 40, the light enters into exit lightguide 42. Exit lightguide 42 is then inserted into ocular tissue 44 to provide illumination for surgical procedures.

Unlike the fifty (50) hour life span of a tungsten light source, the illumination system of the present invention contemplates a life span of approximately twenty thousand (20,000) hours. Accordingly, the present invention provides increased reliability over tungsten light sources due to increased life span, less heat generated as compared to tungsten light sources, and the ability to select a color output in an ophthalmic illumination system by inputing a color output selection into a user interface.

In view of the foregoing, it will be seen that the several advantages of the invention are achieved and attained.

The embodiments were chosen and described in order to best explain the principles of the invention and its practical application to thereby enable others skilled in the art to best utilize the invention in various embodiments and with various modifications as are suited to the particular use contemplated.

As various modifications could be made in the constructions and methods herein described and illustrated without departing from the scope of the invention, it is intended that all matter contained in the foregoing description or shown in the accompanying drawings shall be interpreted as illustrative rather than limiting. For example, condensing lenses may be eliminated such that the LEDs 32, 34, and 36 emit light directly to mixing device 40. Alternatively, mixing device 40 may simultaneously incorporate a condensation of light from LEDs 32, 34, and 36 without the use of a separate condensing lens elements 50, 52, and 54. Thus, the breadth and scope of the present invention should not be limited by any of the above-described exemplary embodiments, but should be defined only in accordance with the following claims appended hereto and their equivalents.

What is claimed is:

1. An ophthalmic illumination system comprising:
   a first light emitting diode;
   a second light emitting diode;
   a third light emitting diode;
   a mixing device for mixing light emitted from said first, second and third light emitting diodes together; and
   an exit lightguide in light communication with said mixing device, said exit lightguide adapted for insertion into ocular tissue.

2. An ophthalmic illumination system according to claim 1, wherein said first light emitting diode emits the color blue, said second light emitting diode emits the color green, and said third light emitting diode emits the color red.

3. An ophthalmic illumination system according to claim 1, wherein said first light emitting diode emits the color blue, said second light emitting diode emits the color yellow, and said third light emitting diode emits the color red.

4. An ophthalmic illumination system according to claim 1, further comprising:
   a first condensing lens in light communication with said first light emitting diode and said mixing device;
   a second condensing lens in light communication with said second light emitting diode and said mixing device; and
   a third condensing lens in light communication with said first light emitting diode and said mixing device.

5. An ophthalmic illumination system according to claim 1, further comprising:
   a user interface for permitting a user to input a desired color output;
   a controller connected to said user interface for determining how much light should be emitted from each of said light emitting diodes to produce the desired color output;
   a first gain amplifier connected to said first light emitting diode;
   a second gain amplifier connected to said second light emitting diode;
   a third gain amplifier connected to said third light emitting diode;
   said controller connected to said first gain amplifier, said second gain amplifier, and said third gain amplifier; and
   whereby said controller sends a first gain signal to said first gain amplier, a second gain signal to said second gain amplifier, and a third gain signal to said third gain amplifier to adjust the output of each of said light emitting diodes to produce the desired color output.

\* \* \* \* \*